United States Statutory Invention Registration [19]

[11] Reg. Number: H918

Andrews et al. [43] Published: May 7, 1991

[54] DECARBONYLATION AND DEHYDROGENATION OF CARBOHYDRATES

[75] Inventors: Mark A. Andrews, Ridge, N.Y.; Stephen A. Klaeren, Corpus Christi, Tex.

[73] Assignee: The United States of America as represented by the United States Department of Energy, Washington, D.C.

[21] Appl. No.: 253,641

[22] Filed: Oct. 5, 1988

[51] Int. Cl.[5] ..... C07D 307/02

[52] U.S. Cl. ..... 549/497; 549/503; 568/853; 568/863

[58] Field of Search ..... 549/497, 503; 568/863, 568/853

[56] References Cited

U.S. PATENT DOCUMENTS

| | | | |
|---|---|---|---|
| Re. 32,084 | 2/1986 | Hoetz | 568/863 |
| 4,089,871 | 5/1978 | Lillwitz | 549/492 |
| 4,197,414 | 4/1980 | Hartwell et al. | 568/852 |
| 4,433,184 | 2/1984 | Huibers et al. | 568/863 |
| 4,487,980 | 12/1984 | Arena | 568/863 |
| 4,540,836 | 9/1985 | Fenton | 568/852 |

OTHER PUBLICATIONS

Y. Nakamura, et al., *Bull. Chem. Soc., Jpn.*, "The Dehydration of D-Fructose to 5-Hydroxymethyl-2-Furaldehyde," 53, 3705-3706, (1980).

P. Collins, *Chem. Communications, "Photochemically Induced Ring Contraction, a Furanoid Ring from a Pyranosidulose," pp. 403-405 (1968).*

S. Rajagopal, et al., *J. Mol. Cat.*, "Deactivation of $RuCl_2(PPh_3)_3$ during Disproportination of D-Glucose in Amide Solvents," 22, pp. 131-135 (1983).

W. M. Kruse, et al., *Carbohyd. Res.*, "Homogeneous Catalytic Hydrogenation of Sugars," 64, pp. 293-296 (1978).

R. Whistler, et al., *J. Org. Chem., "Photolysis of Penta-O-Acetyl-Aldehyde-D-Glucose," 36(17), pp. 2575-2576, (1971).*

S. Pillari, et al., *J. Mol. Cat.*, "Dichlorotris(Triphenylphosphine) Ruthenium (II) Catalyzed Dehydrogenation . . . ," 16, pp. 349-358, (1982).

D. Ward, et al., *Chemistry and Industry, "Decarbonylation of Aldehyde Sugar Derivative . . . " pp. 162-163, (1976).*

*Chemical Abstracts*, 93: 26260e, "Hydroxymethylfurfuryl" (1980).

K. Kaneda, et al., *Chemistry Letters*, "Decarbonylation of $\alpha$ & $\beta$-Diketones Catalyzed by Rhodium Compounds," pp. 215-216 (1974).

Domazeti's, *J. Chem. Comm.*, "Catalytic Decarbonylation of Aldehydes . . . ," pp. 939-940, (1980).

K. Ohno, et al., *J. Am. Chem. Soc.*, "Organic Snythesis by Means of Noble Metal Compounds," 90(1), pp. 99-107, (1968).

S. Maple, et al., *J. Am. Chem. Soc.*, "Detailed Tautomeric Equilibrium of Aqueous D-Glucose," 109, pp. 3168-3169 (1987).

M. MacCoss, et al., *Tetrahedron Letters*, "Synthesis of All Four Possible Isomers of the Acyclonacleoside . . . ," 26(36), pp. 4287-4290 (1985).

M. Baird, et al., *J. Chem. Soc. (A)*, "The Decarbonylation of Aldehydes by . . . ," pp. 348-351 (1968).

D. Doughty, et al., *J. Am. Chem. Soc.*, "Catalytic Decarboylation of Aldehydes," 100(22), pp. 7083-7085, (1978).

L. Lillwitz, *Chemical Abstracts:* 89: 129386x, "Furfuryl Alcohol," (1978).

*Primary Examiner*—Robert L. Stoll
*Assistant Examiner*—Joseph D. Anthony
*Attorney, Agent, or Firm*—Margaret C. Bogosian; James W. Weinberger; William R. Moser

[57] ABSTRACT

Carbohydrates, especially aldose or ketose sugars, including those whose carbonyl group is masked by hemiacetal or hemi-ketal formation, are decarbonylated by heating the feed carbohydrate together with a transition metal complex in a suitable solvent. Also, primary alcohols, including sugar alditols are simultaneously dehydrogenated and decarbonylated by heating a mixture of rhodium and ruthenium complexes and the alcohol and optionally a hydrogen acceptor in an acceptable solvent. Such defarbonylation and/or dehydrogenation of sugars provides a convenient procedure for the synthesis of certain carbohydrates and may provide a means for the conversion of biomass into useful products.

8 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

DECARBONYLATION AND DEHYDROGENATION OF CARBOHYDRATES

This invention was made with Government support under contract number DE-AC02-76CH00016, between the U.S. Department of Energy and Associated Universities, Inc. The Government has certain rights in the invention.

BACKGROUND OF THE INVENTION

The present invention relates to the decarbonylation of carbohydrates, including sugars, and to the simultaneous in-situ dehydrogenation and decarbonylation of alcohols, including sugar alcohols.

Metal complexes such as chlorotris(triphenylphosphine) rhodium and related compounds have been known to be useful as aldehyde decarbonylation agents. See, for example, U.S. Pat. No. 4,089,871; Osborn, J. A., et al., *Inorg. Syn.*, 10:67–71 (1967); Baird, M. C., et al., *J. Chem. Soc. (A)*, 348–351 (1968); Okno, K., et al., *J. Am. Chem. Soc.*, 90:99–107 (1968); and Doughty, D. H., et al., *J. Am. Chem. Soc.*, 100:7083–7085 (1978). However, insofar as these materials have been used in the decarbonylation of carbohydrates, their use has been limited to the decarbonylation of protected sugars. See, for example, Ward, D. J., et al., *Chem. Ind.*, 162–163 (1976); Iley, D. E., et al., *J. Am. Chem. Soc.*, 97:2563–2565 (1975); and MacCoss, M., et al., *Tetrahedron Let.*, 26:4287–4290 (1985). See, also, Kruse, W., et al., *Carbohyd. Res.*, 64:293–296 (1978) and Rajagopal, S., et al., *J. Mol. Catal.*, 22:131–135 (1983), which suggest the deactivation of the hydrogenation catalyst $RuCl_2(PPh_3)_3$ by the decarbonylation of glucose, but which do not identify the resulting sugar products.

This apparent prior limitation of the use of metal complexes to the decarbonylation of protected sugars is not surprising since: (a) it is difficult to find a common solvent for both free (unprotected) sugars and metal complexes that is sufficiently non-coordinating to prevent inhibition of the metal complexes and; (b) since most sugars exist in non-reactive cyclic hemi-acetal and hemi-ketal forms. In this latter regard, for example, it is known that the equilibrium composition of aqueous glucose is 99+% hemi-acetal and only about 0.002% free aldehyde sugar at room temperature. See, for example, Maple, S. R., et al., *J. Am. Chem. Soc.*, 109:3168–3169 (1987) and Angyal, S. J., *Adv. Carbohydr. Chem. Biochem.*, 42:15–68 (1984).

SUMMARY OF THE INVENTION

It is an object of the present invention to provide an improved process for the decarbonylation of carbohydrates using a transition metal complex decarbonylation agent.

Another object of the present invention is to provide a process for the simultaneous in-situ dehydrogenation and decarbonylation of alcohols, particularly sugar alcohols, using a mixture of two or more transition metal complexes and a hydrogen acceptor. One possible long term application of this process is to provide an ecologically sound process for the conversion of biomass into syn-gas or other valuable chemical end products.

These and other objects and advantages of the invention are accomplished in one aspect by mixing a carbohydrate, such as an unprotected aldose sugar or ketose sugar, together with a transition metal complex decarbonylation agent, such as chlorotris(triphenylphosphine)rhodium, in a polar solvent, such as an N-methyl-2-pyrrolidinone, and heating the mixture to a temperature of from about 75° to about 150° C. for at least about 20 minutes, and usually about 1–12 hours, under nitrogen or another inert gas.

In another aspect, the objects of the invention are achieved by mixing together in a suitable solvent an alcohol, such as a sugar alcohol, a hydrogen acceptor, such as cyclooctene, and a mixture of a transition metal complex dehydrogenation agent such as dichlorotris(triphenylphosphine)ruthenium, and a transition metal complex decarbonylation agent such as chlorotris(triphenylphosphine)rhodium, and heating the resulting mixture under a nitrogen or other inert atmosphere at a temperature of about 110°–140° C. for at least about 12 hours and usually from about 1–5 days to effect a simultaneous in-situ dehydrogenation and decarbonylation. Suitable solvents for this purpose include amides, such as N-methyl-2-pyrrolidinone.

DESCRIPTION OF PREFERRED EMBODIMENTS

In its simplest form, the present invention is a process for the decarbonylation of carbohydrates, using a transition metal complex decarbonylation agent. Another aspect of the invention is the use of one or more transition metal complexes and optionally a hydrogen acceptor to effect both the dehydrogenation and decarbonylation of alcohols, specifically carbohydrate (sugar) alcohols.

Pertaining to the first aspect of this invention, aldose or ketose sugars are decarbonylated by treating the sugar with a transition metal complex in a suitable solvent. For example, glucose, an aldose sugar, is smoothly decarbonylated by reacting it with a chlorotris(triphenylphosphine)rhodium decarbonylation agent in N-methyl-2-pyrrolidinone solvent at 75°–150° C., in order to produce arabinitol, a sugar alcohol. Similarly, fructose, a ketose sugar, yields furfuryl alcohol when treated in a similar manner.

The aldose and ketose sugars that may be used as the starting material in the process of this invention are monosaccharide carbohydrates and those di- and oligosaccharides, such as lactose, maltose and cellobiose, which have a hemi-acetal/aldehyde functionality. Monosaccharides are colorless, crystalline solids, or syrups that are soluble in water, but are relatively insoluble in non-polar solvents. These simple sugars contain, in addition to other functionalities such as aldehyde, ketone, amine, etc., the repeating unit $[CH_{20}]_n$, where n equals three or more. The backbone of monosaccharides is an unbranched, or in some cases a branched, single-bonded carbon chain; one of the carbon atoms in this chain is double-bonded to an oxygen atom to form a carbonyl group. If the carbonyl group is at the end of the chain, the monosaccharide is an aldose (containing an aldehyde moiety); if the carbonyl group is at any other position, the monosaccharide is a ketose (containing a ketone moiety). The 4, 5, 6, and 7 carbon-containing aldoses are called, respectively, tetroses, pentoses, hexoses, and heptoses. The pentose xylose, the hexose, glucose, and hexulose fructose, are the most abundant monosaccharides in nature.

Also included within the scope of this invention are the monosaccharides with four or more carbons occurring in cyclic or ring formations, e.g. the hemi-acetal and hemi-ketal sugars. The common cyclic forms of sugars are furanoses (5 member ring) and pyranoses (6 member ring), for example, glucopyranose. The hemiacetal and hemi-ketal forms of the sugar are formed by an intramolecular condensation of a hydroxyl group and an aldehyde or keto carbonyl group, respectively.

The decarbonylation agent of this invention is a transition metal complex. Suitable transition metal complexes typically have substituted phosphine ligands, such as those taught in the references cited on page 1 of this specification. A preferred group of decarbonylation agents are halogen-containing triphenylphosphine transition metal complexes, with the most preferred being chlorotris(triphenylphosphine)rhodiums. Another preferred decarbonylation agent is the dimer complex dichlorotetrakis(triphenylphosphine)dirhodium. Examples of still other suitable decarbonylation agents include, but are not limited to, chlorotris(diphenylmethylphosphine)rhodium, $RuCl_2(PPh_3)_3$, and $[Rh(Ph_2PCH_2CH_2CH_2PPh_2)_2]^+$.

A decarbonylation agent or a mixture of such agents will be used in quantities sufficient to effect decarbonylation. In one preferred embodiment, at least about 0.5 to 2 equivalents, most preferably one equivalent, of the transition metal complex decarbonylation agent are used per equivalent of starting sugar.

The process of this invention can be used to selectively decarbonylate sugars and other carbohydrates by removing a carbon monoxide from the sugar. For example, when the preferred chlorotris(triphenylphosphine)rhodium decarbonylation agent is used, carbon monoxide is trapped by the rhodium complex to form chlorocarbonylbis(triphenylphosphine)rhodiums.

The solvents used in the practice of this invention are solvents which are polar enough to dissolve the sugar, but is sufficiently non-coordinating to permit the transition metal complex to function effectively. Also, solvents must be free of potential CO-donating impurities. If the substituted phosphine component of the metal complex has a strong polar substituent, such as a sulfonate ion, the metal complex could be water soluble; in such a case water could then serve as the solvent. Amide solvents, except for formamides, are especially acceptable solvent systems, with N-methyl-2-pyrrolidinone (NMP) and dimethylacetamide being preferred. Examples of other suitable solvents include but are not limited to glyme ethers and sulfolane.

The decarbonylation reaction must be carried out in the presence of nitrogen, or another inert gas, at a temperature in the range of 75°–150° C., typically about 130° C. for a period of from 20 minutes to about 48 hours, typically from about 1 to 12 hours. Conducting the process according to the present invention results in about 70% to about 100% of the sugar alcohol product.

As noted above, another preferred aspect of this invention relates to the simultaneous in-situ dehydrogenation and decarbonylation of primary alcohols, including sugar alcohols, by a one-step process comprising treating the alcohol with a transition metal complex decarbonylation agent and a transition metal complex dehydrogenation catalyst, and optionally a hydrogen acceptor in a suitable solvent. This one-step process preferably is performed under nitrogen or other inert gas. If sugar alcohols are used as the feed material, the process results in the production of alcohols having fewer carbon atoms than the starting alcohol. Simple primary alcohol feed stocks yield alkanes having one less carbon atom; for example decanol yields nonane.

The dehydrogenation catalysts appropriate for use in this invention are well known in the art and include, for example, dichlorotris(triphenylphosphine)ruthenium and carbonylbistrifluoroacetatebis(triphenylphosphine)ruthenium. When carbonylbistrifluoroacetatebis(triphenylphosphine)ruthenium is used as the dehydrogenation catalyst, no hydrogen acceptor is needed. The ruthenium dehydrogenation catalyst may be used in conventional catalytic amounts, and may be substituted for by other known dehydrogenation catalysts. Other dehydrogenation catalysts which may be used in the present invention include, for example, $HRh(PPh_3)_4$, $H_2Ru(PPh_3)_4$, and even $RhCl(PPh_3)_3$ itself.

The dehydrogenation catalyst normally will be used in amounts ranging from about 0.1 to 100, preferably 1 to about 10 mole percent, based on the moles of alcohol being converted.

The hydrogen acceptors suitable for use in this aspect of the invention are well known and include, for example, cyclooctene, benzalacetone, benzalacetophenone, and styrene.

This aspect of the invention can be exemplified by the treatment of glucitol under nitrogen with $RhCl(PPh_3)_3$ alone or a mixture of the ruthenium and rhodium complexes noted above, and a hydrogen acceptor such as cyclooctene, in N-methyl-2-pyrrolidone solvent to yield a mixture of furfuryl alcohol, the five-carbon sugar alcohols arabinitol and xylitol, and smaller amounts of the four carbon sugar alcohols erythritol and threitol.

The alcohols which can be dehydrogenated and decarbonylated in accordance with this aspect of the present invention include sugar alcohols, as well as simple alkanols and glycols. Examples of suitable primary alcohol starting materials include, but are not limited to, 1,2-propanediol, glucitol, mannitol, arabinitol, xylitol, furfuryl alcohol, erythritol, threitol, and 1-decanol. Since aldose sugars are decarbonylated to sugar alcohols under these reaction conditions, aldose sugars may also serve as feedstocks for this process.

The decarbonylation reaction, and the simultaneous in-situ dehydrogenation and decarbonylation reactions can be carried out either batchwise or continuously. In any of these methods, the transition metal complex(es) can be recycled. In recycling the used complex(es), a fresh supply of the complex(es) may be added.

The desired alcohol can be separated and recovered from the reaction mixture by customary methods. Any conventional separating methods can be used for this purpose. For example, after the reaction has been completed, the liquid phase may be distilled or extracted to recover desired products. In one embodiment, the amide solvent is evaporated and the resulting solid is partitioned between chloroform/water. The metal complex will migrate to the chloroform and the sugar will dissolve in the water phase, from which it can be recovered by evaporation of the water.

Although the above description of the invention includes a recitation of preferred embodiments, this is not intended to limit the invention.

The following Examples illustrate the present invention more specifically.

EXAMPLE 1

In a typical reaction, sugar (150 μmol) and $RhCl(PPh_3)_3$ (150 μmol) are dissolved in N-methyl-2-pyrrolidinone (NMP) (Aldrich HPLC grade, 5 mL) and heated under nitrogen at 130° C. until the solution becomes yellow or no further color change is observed. Sugar products are identified and quantitated by FID capillary GC after silylation of an aliquot of the reaction mixture with trimethylsilylimidazole/pyridine (Pierce Chemical). Identifications are confirmed by GC-MS and/or $^1H$ or $^{13}C$ NMR. $Rh(CO)Cl(PPh_3)_2$ is identified and quantitated by IR (yield >90% in almost all cases). The carbonyl complex can be recycled to $RhCl(PPh_3)_3$. Dimethylacetamide or other suitable solvents may be used in place of NMP. Small amounts of water do not interfere, but solvents must be free of potential CO donating impurities.

One method of ascertaining that the solvent is free of impurities is by heating $RhCl(PPh_3)_3$ alone in the solvent and comparing the intensity of the 1977 $cm^{-1}$ CO stretch of the resulting $Rh(CO)Cl(PPh_3)_2$ vs. a standard solution. The NMP used here gave $\leqq 1$ μmol $Rh(CO)Cl(PPh_3)_2$/ml after 48 hr at 130°, indicating that it is pure.

EXAMPLES 2-6

Using the above described procedure of Example 1, glucose (Example 2) was cleanly decarbonylated by one equivalent of chlorotris(triphenylphosphine)rhodium to yield arabinitol (88%) in about 4 hours. Similarly, arabinose (Example 3) yielded erythritol (84%). Glyceraldehyde (Example 4), which has a higher free aldehyde content (ca. 2% in aqueous solution at room temperature), yielded ethylene glycol (95%) in just 30 minutes under the same conditions. Similar results were observed with glycol aldehyde, which yielded methanol (83%) and glucoheptose which yielded glucitol (88%) (Example 5). A practical demonstration of the utility of this reaction is provided by the one-step conversion of commercially available 2-deoxyribose (Example 6) into the much less accessible 1-deoxyerythritol (30 min., >90%). This is particularly significant in that the best known synthesis of 1-deoxyerythritol requires seven steps from glucose [Chaby, R., et al., *Tetrahedron*, 27:3197-3205 (1971)].

EXAMPLES 7-8

Ketose sugars can also be readily decarbonylated using the process of this invention. Thus, fructose (Example 7) yielded furfuryl alcohol as the major product (2 hours, 79%), while 1,3-dihydroxyacetone (Example 8) reacted with excess chlorotris(triphenylphosphine)rhodium to give about 1.8 to 1.9 equivalents of carbonylchlorobis(triphenylphosphine)rhodium and methane (8 hours, >90%).

EXAMPLE 9

In a typical combined dehydrogenation/decarbonylation, 1-decanol (398 μmol) was treated with $RuCl_2(PPh_3)_3$ (19 μmol), $RhCl(PPh_3)_3$ (96 pmol) and benzalacetophenone (438 pmol) in 2 ml of N-methyl-2-pyrrolidinone and heated under nitrogen at 125° C. After 40 hours, 64 μmol of nonane had formed; after 6 days the yield of nonane was 92 μmol (96% based on Rh).

While particular embodiments of the invention have been described, it will be understood, of course, that the invention is not limited thereto, and that many obvious modifications and variations thereof can be made, and that such modifications and variations are intended to fall within the scope of the appended claims.

We claim:

1. A process for the decarbonylation of an aldose or kitose sugar, each of said sugars having unprotected alcohol moieties, comprising the steps of:

(a) dissolving said sugar in a solution containing a transition metal complex decarbonylation agent, selected from the group consisting of chlorotis(triphenylphosphine)rhodium, dichlorotetrakis(triphenylphosphine) dirhodium, chlorotris(diphenylmethylphosphine)-rhodium, $[Rh(Ph_2PCH_2CH_2PPH_2)_2]^-$, and mixtures thereof, and a suitable aprotic, polar solvent free of CO-donating impurities, under an inert atmosphere; and (b) heating the carbonyl-free solution containing the dissolved sugar which results from step (a) for a time sufficient to effect decarbonylation of said sugar while maintaining said inert atmosphere.

2. The method of claim 1 wherein the decarbonylation process is conducted under nitrogen.

3. The process of claim 1, wherein said aldose sugar is selected from the group consisting of glucose, arabinose, glyceraldehyde, 2-deoxyribose, glucoheptose and glycol aldehyde.

4. The process of claim 1 wherein said ketose sugar is selected from the group consisting of fructose and 1,3-dihydroxyacetone.

5. The process of claim 1 wherein said sugar is an unprotected sugar existing predominantly in the form of a hemi-acetal or a hemi-ketal.

6. The process of claim 1 wherein the resulting mixture is heated to a temperature in the range of from about 75° C. to about 150° C.

7. The process of claim 1 wherein said suitable solvent is selected from the group consisting of polar amide solvents.

8. The process of claim 7 wherein said solvent is selected from the group consisting of N-methyl-2-pyrrolidinone and dimethylacetamide.

* * * * *